United States Patent
Thomas et al.

(10) Patent No.: US 7,318,059 B2
(45) Date of Patent: *Jan. 8, 2008

(54) HEALTHCARE ORGANIZATION RECORD IDENTIFIER ASSIGNMENT MANAGEMENT SYSTEM

(75) Inventors: Denise Marie Thomas, Salt Lake City, UT (US); Gaylene Curtis, Taylorsville, UT (US); John E. Grant, Layton, UT (US)

(73) Assignee: Siemens Medical Solutions Health Services Corporation, Malvern, PA (US)

( * ) Notice: Subject to any disclaimer, the term of this patent is extended or adjusted under 35 U.S.C. 154(b) by 200 days.

This patent is subject to a terminal disclaimer.

(21) Appl. No.: 11/256,865

(22) Filed: Oct. 24, 2005

(65) Prior Publication Data

US 2006/0036468 A1 Feb. 16, 2006

(51) Int. Cl.
*G06F 17/30* (2006.01)
*G06F 15/16* (2006.01)

(52) U.S. Cl. .................... 707/3; 707/4; 707/5
(58) Field of Classification Search .......... 707/3, 707/4, 5
See application file for complete search history.

(56) References Cited

U.S. PATENT DOCUMENTS

| | | | |
|---|---|---|---|
| 5,579,393 A | 11/1996 | Conner et al. | |
| 5,819,263 A | 10/1998 | Bromley et al. | |
| 5,838,967 A | 11/1998 | Okayama et al. | |
| 6,018,713 A | 1/2000 | Coli et al. | |
| 6,163,781 A | 12/2000 | Wess, Jr. | |
| 6,269,379 B1 | 7/2001 | Hiyama et al. | |
| 6,978,268 B2 * | 12/2005 | Thomas et al. | 707/10 |
| 2001/0044731 A1 | 11/2001 | Coffman et al. | |
| 2001/0051879 A1 | 12/2001 | Johnson et al. | |
| 2001/0051880 A1 | 12/2001 | Schurenberg et al. | |
| 2002/0007284 A1 | 1/2002 | Schurenberg et al. | |
| 2002/0026381 A1 | 2/2002 | Sasaki | |
| 2002/0059300 A1 | 5/2002 | Nagata et al. | |
| 2003/0176785 A1 | 9/2003 | Buckman et al. | |
| 2003/0177132 A1 | 9/2003 | Thomas et al. | |
| 2006/0010015 A1 * | 1/2006 | Thomas et al. | 705/3 |

* cited by examiner

Primary Examiner—Jeffrey Gafrin
Assistant Examiner—Tony Mahmoudi
(74) Attorney, Agent, or Firm—Alexander J. Burke

(57) ABSTRACT

A system (100) for providing multiple facility healthcare corporations the ability to assign and maintain shared medical record numbers (43) across multiple entities. The system establishes a parent/child relationship among the entities to share medical record number ranges, formats, and data. A patient record identifier database (102) contains patient records in a searchable unit record file (50) and an identification number file (3). A search processor (105) locates relevant records and a rules processor (104) applies various tests to the returned data in order to assign a medical record number (43, 13) to a single unique unit reference number (2, 5, 11) to a person without duplication or conflict with identifiers used at other entities (4, 9, 190). The reference numbers and their associated medical records are shared among the various entities. The sharing relationships may be altered by authorized users accessing on line file maintenance (312) and programs (311).

17 Claims, 12 Drawing Sheets

| | Facility One Admitting or Current Facility Medical Record Number | Facility Two Medical Record Number | Facility Three Medical Record Number |
|---|---|---|---|
| 201 | None | None | None |
| 202 | 99-99-99 | None | None |
| 203 | None | 99-99-99 | None |
| 204 | 99-99-99 | 88-88-88 | None |
| 205 | None | 88-88-88 | 77-77-77 |
| 206 | 99-99-99 | 88-88-88 | 77-77-77 |
| 207 | None but 99-99-99 exists. | 99-99-99 | None |

```
===================================================================
GP0310RU    18       GENERAL PURPOSE              MS4DEV
22.20             Table File Maintenance           4/26/02
DTHOMAS                                           12:54:04
===================================================================
Table: MREDIT     MEDICAL RECORD NUMBER CONTROLS Element............  10 ──210
  Description........  UTAH ──211
                                  ──212
  Short Description..  UTAH
  Field-1............  99-99-99 ──213
  Field-2............  N                         17
  Field-3............           ──214
  Field-4............  T
  Field-5............           ──215
  Field-6............

Amount 1...........      .00      Amount 2.....    .00
  Quantity 1.........        0      Quantity 2...      0
  Date 1.............               Date 2.......

Revised By.........  DTHOMAS  2/26/2002  Status....... A

F3=Exit    F12=Previous

```
===================================================================
GP3500RU 01                General Purpose             MS4DEV
22.20                    Next MR# Maintenance          4/26/02
DTHOMAS                         19                    13:37:54
===================================================================
                    ──183
Position to: Entity Mnemonic or Number _____

Type options, press Enter.              ──54
  2=Change   4=Delete   9=Assign Sharing Entity
                                              ──182
  Opt Entity# Description            Mnem  Sharing Description       Mnem
                               ──181         Entity#
  ──00020 SALT LAKE MEDICAL CENT SALT  00010 UTAH MEDICAL CENTER    UTAH
     00010 UTAH MEDICAL CENTER    UTAH        ──220              185 ──

Bottom
  F3=Exit   F5=Refresh   F6=Add   F12=Previous
===================================================================
```

Fig. 5

```
GP3500RU 02              General Purpose                        MS4DEV
22.20                   Next MR# Maintenance                    4/26/02
DTHOMAS                 UTAH MEDICAL CENTER      51             13:45:23
==================================================================================
                                            20

From MR#      To MR#       Next MR#     Revision Date   Revision ID
00-00-00      99-99-99     00-01-03     02/25/2002      DTHOMAS
    21           22            23

```
===============================================================================
    PHDE010A                    ONLINE PATIENT REGISTRATION            4/03/02
                              Patient History and Accounting    73    17:36:49

Relationship............. REGISTRANT
Name (Lst,Fst,Mid,Sfx)... THOMAS             DENISE          MARIE
Add Name,Title...........
Address Line 1, Line 2... 10240 SOUTH 900 EAST
City/State/Zip/County ... SALT LAKE CITY        UT 84119
Country.................. USA                              Home Phone 801 8889696
Birth Date & Place....... 12/31/1972 AMERICAN FORK            SSN#      898986892
Sex ..................... F
Marital Status........... S       Living Will...............  Date   0/00/00
Religion & Church........ LDS     Durable Power of Attorney.  Date   0/00/00
Race Code (Observe)...... W       VIP Code..................
Employer # or Name.......         SIEMENS                             Dpt
Work Phone............... 801 5689888   Ext 4744
Occupation............... SENIOR ANALYST        Employee Num...
Date Employment Began.... 09/01/1985            Employment Status........ 1
Family Physician.........       *NONE           Confidential Record......
Med Rec #................ *CALC                 Radiology Indx
FLAG 1    74     LANGUAGE       FLAG 3       FLAG 4          FLAG 5
FLAG 6           FLAG 7    72   NOTE
F3=Exit    F11=Alt Addr    F12=Prev    F15=Prev Name    F24=More Keys
===============================================================================
```

Fig. 8

```
GP3500RU 02                General Purpose                    MS4DEV
VERSION      187          Next MR# Maintenance                10/10/YY
USERID                    REGIONAL MEDICAL CENTER              1:07:43
================================================================

Type Options, Press Enter.
2=Change    4=Delete

Opt    From MR#      To MR#        Next MR#
       00-00-01      39-99-99      00-00-31

197

186   196
                                                          194
                                                                  Bottom
              F3=Exit    F5=Refresh    F6=Add    F12=Previous
```

Fig. 10

```
GP3500RU 03                General Purpose                    MS4DEV
VERSION                   Next MR# Maintenance                10/10/YY
USERID                    REGIONAL MEDICAL CENTER             11:17:35
================================================================

From MR#     To MR#      Next MR#     Revision Date   Revision ID
00-00-01     39-99-99    00-00-31     02/15/2002      USERID 196         197         198            199            200

195

Bottom
    F3=Exit    F5=Refresh    F12=Previous
```

Fig. 11

```
GP3500RU 06              General Purpose                    MS4DEV
VERSION                  Entity Search                      10/10/YY
USERID                                                      10:31:28
================================================================

Entit┌─────────────────────────────────────────────────────┐
     │           Confirm delete of Sharing Entity          │
Posit│                                                     │
     │     Press F14 to confirm delete or F12 to cancel.   │
Type │                                                     │
     │     Entity#   Description                  Mnem  Sts│
  1=Se│    00100    UTAH COUNTY HOSPITAL          UTAH   A │
     │                                                     │
Opt  │                                         214         │
     │                                                     │
 __  │                                                     │
     │                                                     │
     │     F12=Cancel    F14=Confirm Delete                │
     │                                    ─215             │
     └─────────────────────────────────────────────────────┘
                                                     Bottom
F3=Exit   F5=Refresh   F12=Previous
```

Fig. 17

```
GP3500RU 05              General Purpose                    MS4DEV
VERSION                Next MR# Maintenance                 10/10/YY
USERID                                                      11:10:05
================================================================
                         ─193
Entity Mnemonic:  ____

From MR#         To MR#          Next MR#             188
_____       _____       _____

_____       _____       _____

_____       _____       _____

_____       _____       _____
       ─190            ─191             ─192

More...
F3=Exit   F4=Prompt   F5=Refresh   F12=Previous
```

Fig. 18

HEALTHCARE ORGANIZATION RECORD IDENTIFIER ASSIGNMENT MANAGEMENT SYSTEM

This is a non-provisional application of provisional application Ser. No. 60/364,539 by D. M. Thomas et al. filed Mar. 16, 2002.

FIELD OF THE INVENTION

This invention relates generally to a record keeping and database organization system, and more specifically to a system that permits multiple facility healthcare corporations to assign and maintain shared medical record numbers across multiple entities.

BACKGROUND OF THE INVENTION

The healthcare industry has traditionally suffered from information fragmentation. Frequently, multiple medical record numbers are assigned to a patient who is cared for by each of several facilities within a multiple facility hospital organization, creating high volumes of duplicate medical record numbers and causing other waste of, e.g. prelabeled folders. Maintaining decentralized or multiple Medical Records Departments within a multientity organization causes additional overhead costs. This practice results in multiple medical record numbers being assigned to a patient who is cared for by several facilities, inevitably causing confusion regarding a patient's medical record data. The workflow of hospital personnel is often less accurate due to the multiple locations of patient medical record information. Impaired access to complete patient information hinders a physician's ability to properly treat the patient.

Numerous attempts have been made to simplify the collection and integration of medical records by a large healthcare provider. One method is to surrender to the multiplicity of records and simply attempt to locate all of them at any given moment. For example, U.S. Pat. No. 5,899,998, entitled METHOD AND SYSTEM FOR MAINTAINING AND UPDATING COMPUTERIZED MEDICAL RECORDS, issued on May 4, 1999 to McGauley et al., discloses a device for collecting the medical record data by having each patient carry a portable data storage device such as a "smart card" which is sensed by various point of service stations distributed around the healthcare facility. U.S. Pat. No. 6,333,690, entitled WIDE AREA MULTIPURPOSE TRACKING SYSTEM, issued on Dec. 25, 2001 to Nelson et al., is also related to locating the medical record by means of a radio transmitter or similar device.

Reliance on a computer database to retrieve inherently fragmented data creates additional problems. For example, U.S. Pat. No. 5,974,389, entitled MEDICAL RECORD MANAGEMENT SYSTEM AND PROCESS WITH IMPROVED WORKFLOW FEATURES issued on Oct. 26, 1999 to Clark et al., is related to sharing a computer database, and the problem of preventing simultaneous viewing of medical records by those, such as a pharmacist and a physician, who should be aware of the other's action. Thus, the Clark et al. system insures that records are viewed in a serial fashion. On the other hand, U.S. Pat. No. 6,347,329, entitled ELECTRONIC MEDICAL RECORDS SYSTEM, issued on Feb. 12, 2002 to Evans explicitly permits simultaneous access to fragmented medical records.

Many computer based medical record systems are in fact nothing more than a search engine designed to retrieve multiple, widely dispersed data. U.S. Pat. No. 6,304,848, entitled MEDICAL RECORD FORMING AND STORING APPARATUS AND METHOD RELATED TO SAME, issued on Oct. 16, 2001 to Singer discloses a system of medical records management based on searches of common elements such as medical terms. U.S. Pat. No. 6,263,330, entitled METHOD AND APPARATUS FOR THE MANAGEMENT OF DATA FILES, issued on Jul. 17, 2001 to Bessette provides a network system for storage of medical records. The records are stored in a database on a server. Each record includes two main parts, namely a collection of data elements containing information of a medical nature for a certain individual, and a plurality of pointers providing addresses or remote locations where other medical data for that particular individual resides.

U.S. Patent Application No. 2002/0007284, entitled SYSTEM AND METHOD FOR IMPLEMENTING A GLOBAL MASTER PATIENT INDEX, published on Jan. 17, 2002 and filed by Schurenberg et al., discloses a global master patient index (GMPI). The GMPI performs functions such as locating patient records, locating duplicate records for a selected patient, printing a selected patient record with all its duplicate patient records, reconciling potential duplicate patient records found while searching and retrieving a patient's record, final reconciliation (certification) of suspected duplicate patients records, maintaining a persistent relationship between patient records in the GMPI, and maintaining a reconciliation audit trail.

U.S. Patent Application No. 2001/0051879, entitled SYSTEM AND METHOD FOR MANAGING SECURITY FOR A DISTRIBUTED HEALTHCARE APPLICATION, filed by Johnson et al., discloses a health data network that allows storage of patient record information in a parent/child relationship using a global master patient index to integrate patient record information used either by multiple facility healthcare organizations or by a single business with multiple sites or computer databases.

SUMMARY OF THE INVENTION

The present invention assigns shared medical record numbers across multiple entities. This allows hospitals to assign the same medical record number for a patient throughout their organization, thereby eliminating multiple medical record numbers from being assigned to a patient who is cared for by several different facilities. The present invention reduces the number of duplicate medical record numbers across entities within a multiple facility organization, eliminates the need to maintain multiple Medical Records Departments within a multiple facility organization and improves the accuracy of the medical record number assignment process. A material cost savings will also be realized as duplicate physical record volumes decline.

The present invention simplifies the workflow of hospital personnel by consolidating their work environment. This results in greater accuracy of patient medical information and the possible reduction of staffing costs. The present invention allows data that is associated with one medical record number per patient to be stored in one location, regardless of the number of remote locations the patient has visited within the multiple entity organization. The existence of only one medical record per patient minimizes the need to reconcile duplicate patient records and the need to maintain multiple records is avoided. This invention can be used by hospitals, long term care facilities, skilled nursing facilities, outpatient clinics and physician offices that assign and maintain patient health record numbers.

BRIEF DESCRIPTION OF THE DRAWINGS

FIG. 4 is a pictorial representation of a display by which medical record numbers are assigned when using the system depicted in FIG. 1;

FIG. 5 is a pictorial representation of a display in which medical record number relationships are maintained when using the system depicted in FIG. 1;

FIG. 6 is a pictorial representation of a display in which the user of the present invention identifies the range of medical record numbers to be shared with other entities;

FIG. 8 is a pictorial representation of a display used when adding entities to the medical record sharing system of the present invention;

FIG. 10 is a pictorial representation of a display in which the user of the present invention may select an existing subset of medical record numbers;

FIG. 11 is a pictorial representation of a display in which the user of the present invention may update the range of selected medical record numbers;

FIG. 17 is a pictorial representation of a display which permits the deletion of a sharing entity by the user of the present invention; and FIG. 18 is a pictorial representation of a display which permits multiple medical record number ranges to be entered by the user of the present invention.

DETAILED DESCRIPTION OF THE INVENTION

Figures 1, 2:
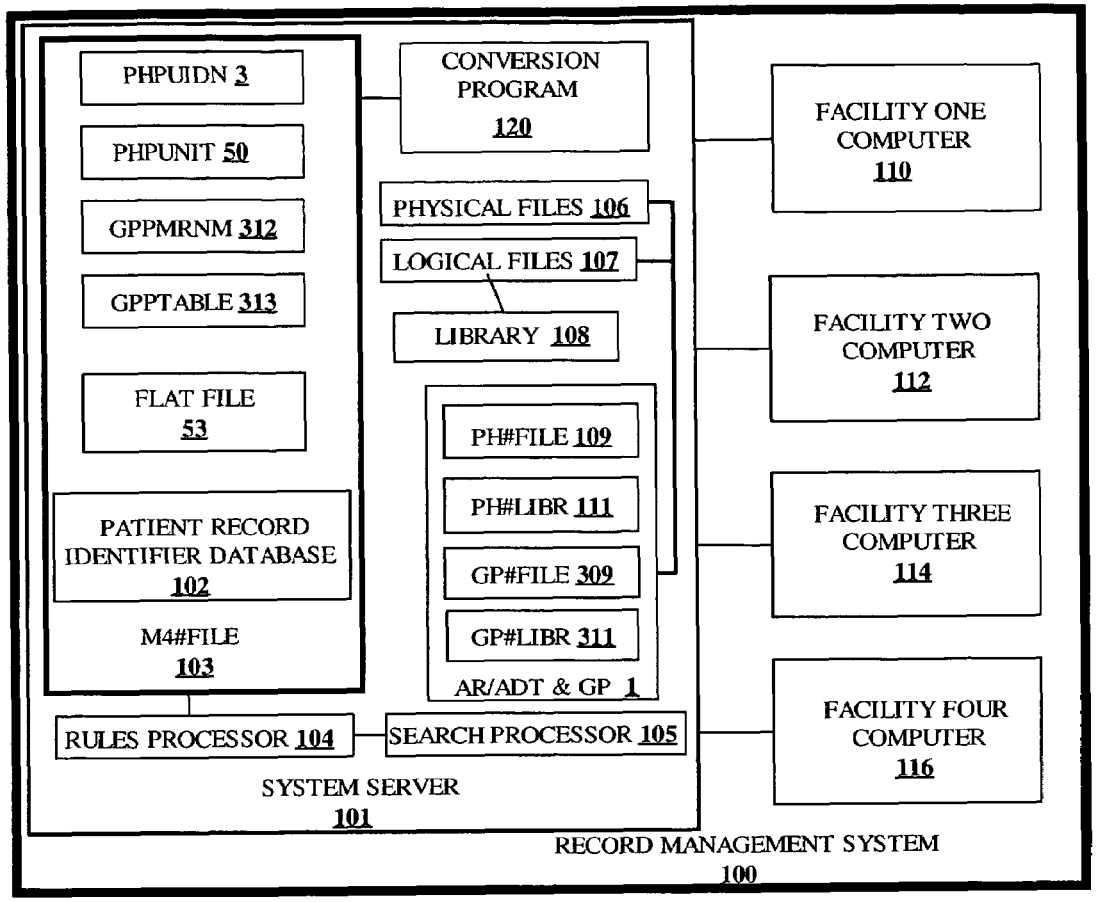
FIG. 1 is a block diagram of a central record management system constructed in accordance with the present invention.
FIG. 2 is a table depicting medical record number scenarios addressed by the central record management system depicted in FIG. 1.

Large corporations having multiple departments, entities, or facilities that maintain a Central Business Office (CBO) can, according to the principles of the present invention, also create a Central Medical Records Department (CMRD). The CMRD environment includes a centralized medical records staff, shared medical record numbers that are available to multiple departments or entities, and a centralized filing system. Referring to FIG. 1, the Record Management System 100 establishes a parent/child relationship among each hospital entity 110, 112, 114 and 116, for example, in order to share medical record number ranges, formats, and data. A child record is an entity record that points to a parent record for the medical record number range. A parent record is an entity record that controls the record number range for other entities, such as child records. A record number range is a medical record number assignment controlled by a series of numbers between a beginning and ending number.

Medical record personnel organize the shared medical record numbers, their associated medical record number format, and their shared number ranges through online file maintenance. The Record Management System 100 includes a system server 101 housing or accessing a patient record identifier database 102, a rules processor 104 for examining the identifiers of database 102 and a search processor 105 which determines for each entity 110, 112, 114 and 116 the identifier associated with a particular patient. The rules processor 104 includes an identifier generator which produces available identification numbers when a new identifier is needed.

Referring also to FIG. 2, the shared medical record number scheme of the present invention addresses several scenarios. While three entities are used in this example, the present invention can accommodate a very large number of separate entitiesor departments. Each scenario is followed by the shared medical record assignment logic that is used by rules processor 104 to address the specific problem posed by each scenario and thereby eliminate the occurrence of duplicate and multiple records for a single patient:

The first scenario 201 is the admission of a patient who does not have a medical record number at any of the other facilities in the hospital. In this situation, the patient will be assigned the lowest available medical record number that has not already been assigned at any of the sharing entities.

The second scenario 202 is the admission of a patient who has a medical record number only at the current facility. In this scenario, the patient will keep the existing medical record number for the current admitting entity.

The third scenario 203 is the admission of a patient who has a medical record number at one of the other two facilities but not the current facility. In this case the patient will be assigned the same medical record number that already exists in any of the other sharing entities.

The fourth scenario 204 is the admission of a patient who has a medical record number at the current facility and a different medical record number at one of the other facilities. The fourth scenario 204 can only exist if historical medical record data was created prior to the implementation of the present invention. In this situation the patient retains the existing medical record number for the current admitting entity.

The fifth scenario 205 is the admission of a patient who has different medical record numbers at other facilities (a relic of a prior record keeping system) but does not have a medical record number in the current facility. The rules processor 104 will cause the patient to be assigned the lowest medical record number of the two existing numbers previously assigned by the other entities.

The sixth scenario 206 is the admission of a patient who has different medical record numbers at all three facilities. This scenario can only exist if historical medical record data was created prior to the implementation of a shared medical record numbers system. In this case the rules processor 104 assigns the patient the existing medical record number for the current admitting entity.

The seventh scenario 207 addresses the admission of a patient who has a medical record number in the second entity and is being admitted to the first entity, but a different patient in the first entity already has the same medical record number. This can happen only if historical medical record data was created prior to sharing medical record numbers. The rules processor 104 does not permit the sharing of the same medical record number between different patients. Hence, a new medical record number will be assigned to the patient by rules processor 104.

The system server 101 includes physical files 106 (e.g. disk drives) within the record management system 100. Multiple database fields are defined in each physical file 106 to store specific data elements. A complete set of the database fields is also referred to as a record. A physical file 106 can contain a number of individual records. System server 101 also utilizes logical files 107 to provide different views of the physical files 106. These physical and logical files 106, 107 are grouped together and stored in (or accessed by) application-specific software libraries 1 and 108, for example, based on the purpose of the software. Libraries 1 and 108 also contain the application-specific program libraries 111, 311 that interact with the files 106 and 107.

For example, the system server 101 includes the Accounts Receivable, Admission, Discharge, Transfer (AR/ADT) and General Purpose (GP) application-specific file and program libraries 1. File libraries 1 contain physical and logical files stored within PH#FILE 109 and GP#FILE 309. Program libraries 1 contain programs stored within PH#LIBR 111 and GP#LIBR 311 which contain the programs that work with the physical and logical files 106, 107, 108 contained in PH#FILE 109 and GP#FILE 309 to provide the features and functionality of the present invention. When a system server 101 user accesses the record management system 100 using either their personal computer or a passive terminal, the management system 100 automatically creates, based on the user profile, a library list containing the specific software applications' file 109, 309 and program 111, 311 libraries the user needs to complete their daily work.

The system server 101 includes a common file library called M4#FILE 103. The file library 103 contains or accesses all of the "shared" or "global" physical and logical files across all system server 101 patient financial applications. Hospitals that belong to a multiple entity corporation who implement a Central Business Office (CBO) share the patient record identifier database 102 located in the physical files in the M4#FILE 103. This is also where the Unit Record File (PHPUNIT) 50, the Unit Identification Number File (PHPUIDN) 3, the Next Medical Record Number Assignment File (GPPMRNM) 312, and the General Purpose Table File (GPPTABLE) 313 reside in order to allow patient identifier number sharing to occur.

Figure 3:
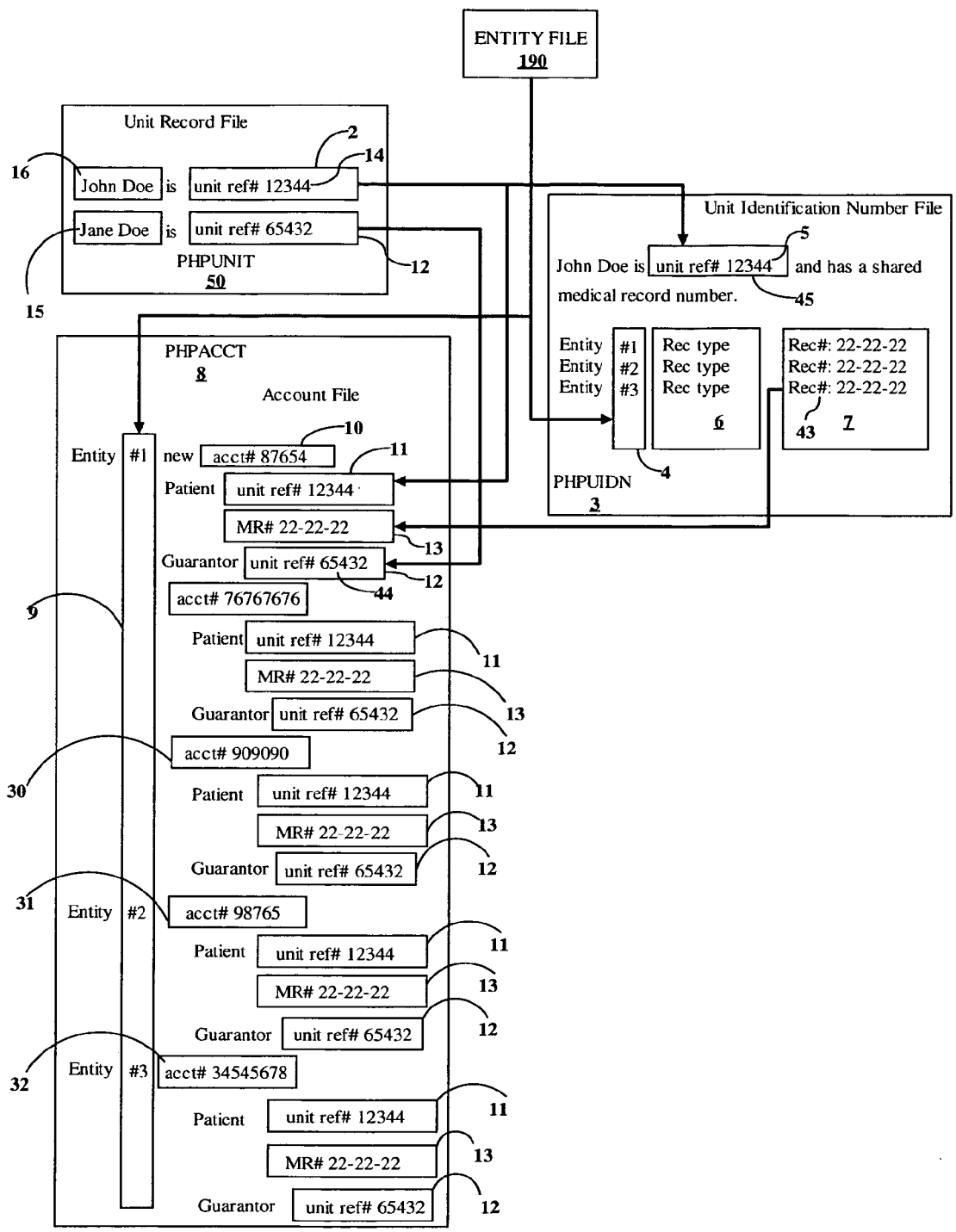
FIG. 3 is a block diagram depicting the linking of shared medical record numbers when using the system depicted in FIG. 1.

Throughout the patient record identifier database 102, unit reference number fields exist in physical files and are used to link relevant data. Referring to FIG. 3, a unit reference number 14 is a unique number generated and assigned to the patient during the registration or admission process. The reference number 14 is maintained in the Unit Record file (PHPUNIT) 50 in the unit ref# (UREF#) field 2. The Unit Record file 50, also referred to as the Master Person Index, is a central repository that stores important demographic information that is unique to that individual. The Master Person Index 50 maintains those unique unit records for each person entered into the record management system 100. In FIG. 3, two such people are illustrated.

The Unit Record Identification Number File (PHPUIDN) 3 contains the following fields:

(a) Entity Code field (IDENT#) 4 identifies which entity within the shared environment created the record.

(b) Unit Reference Number field (IDREF#) 45 contains a unique system generated patient identification number 5 that links the person's demographic information with this particular record.

(c) Identification Num Type field (IDTYPE) 6 identifies the type of record (medical record number versus a radiology number or foreign system identification number).

(d) Identification Number field (IDIDE#) 7 contains the actual medical record number.

The two files PHPUNIT 50 and PHPUIDN 3 can be linked together when the value 14 present in the UREF# field 2 in PHPUNIT 50 is identical to the value 5 residing in the IDREF# field 45 in PHPUIDN 3. If the IDTYPE field 6 in PHPUIDN 3 identifies a medical record number type (MR#), and a medical record number 43 resides in the IDIDE# field 7, then the link to a medical record number is established.

The AR/ADT Account File (PHPACCT) 8 contains the following key fields:

(a) Entity Number field (AENT) 9
(b) Account number field (ACCT#) 10
(c) Patient's Unit Reference Number field (APREF) 11
(d) Guarantor/Relative Unit Reference Number field (AGREF) 12
(e) Medical Record Number field (AMDRC) 13

Each person affiliated with the patient during the registration or admission process also receives his or her own unique unit reference number 44. These unit records include data identifying e.g. the patient's guarantor, the patient's spouse/parent, and the patient's relative. This allows hospitals to service their community and their families by eliminating redundant entry. For unit records belonging to persons that have been patients at any of the facilities, a medical record identification number may also be assigned based on the hospital's choice of which patient types (or services) require medical record numbers. Medical record identification numbers 43 are stored in the Unit Identification Number File (PHPUIDN) 3 in the IDIDE# field 7. Identical fields for both the unit reference number 5 and the medical record number 43 are stored in additional database files which are to be used as links. Additional key fields such as entity code field 4 and account number field 10 are also stored and used as additional links with the unit reference number 5 and the medical record number 7 values in order to define a path to specific information.

The entity code or number associated with the Entity File (GPPENTY) 190 is stored in important entity specific files such as the Account File (PHPACCT) 8, entity code field (ADENT) 9 and the Medical Record Identification File (PHPUIDN) 3, entity code field (IDENT#) 4 and is used in linking entity specific data. The search processor 105 also utilizes the entity field 4 along with the unit reference number field 5, 45 when searching PHPUIDN. Access to specific entities is controlled through the user's profile stored in the system server 101.

During the registration procedure for a patient, the user who in the illustrated embodiment may be the admission clerk, conditions the system to search the Master Person Index 50 using combinations of the patient's last name, first name, middle initial, social security number, and birth date in order to determine if a unit record number 14 already exists for the person (John Doe) 16 in the PHPUNIT file 50. Whether the admission clerk selects an existing unit record or creates a new unit record, the clerk will then condition the system to search for a medical record entry 4, 6, 43 using the search processor 105 and the rules processor 104. The search processor 105 knows which entity 190 is performing the registration based on the admission clerk's profile stored in the system server 101.

If no unit record number 14 is found, a new unit record in the PHPUNIT file 50 is generated linking the patient name (John Doe) 16 to a newly created unit reference number 14 in field 2, and including biographical and demographical information about the new patient. In addition, a medical record entry 4, 6, 7 is created. A medical record number 43 is assigned in field 7 using the assignment scenarios already described for rules processor 104, and a link is established via the new unit reference number 5 in field 45 to the new patient record created for the patient in PHPUIDN 3. At the same time, a new record is created in the PHPACCT file 8 for this entity 9, 190 linking a newly created account record number 10 to the new unit reference number 11 and the new medical record number 13 for the new patient (John Doe) 16 in the PHPUNIT file 50 and the new medical record entry for this entity 4, 6, 7 in the PHPUIDN file 3. This record also associates or links the unit reference number 44 for the guarantor (Jane Doe) 15 with the guarantor's (Jane Doe) unit reference number 12 in the PHPUNIT file 50 and updates the PHPACCT file 8.

If a unit record number already exists in the PHPUNIT file 50 (John Doe) 16, 14 and a medical record entry 4, 6, 43 already exists in the PHPUIDN file 3 the registration continues creating the new record in the PHPACCT file 8 using the same links previously described. If a unit record number already exists in the PHPUNIT file 50 (John Doe) but a medical record entry 4, 6, 43 does not exist in the PHPUIDN file 3, a medical record entry 4, 6 is created, a medical record number 43 is assigned in field 7 using the assignment scenarios already described for rules processor 104, and the registration continues creating the new record in the PHPACCT file 8 using the same links previously described.

A PHPUIDN 3 record with an MR# identification number type 6 will never be created for a patient unless a PHPUNIT 50 record previously exists or is created simultaneously for a new patient. This eliminates the possibility of orphaned, irrelevant, or wasted medical record identification data in PHPUIDN 3.

The Patient Record Identifier Database 102 (FIG. 1) allows medical record numbers 43 to be from one to twelve characters in length. Hospitals define their medical record number format by means of a system 101 file maintenance protocol. The file maintenance protocol allows the hospital to set up the medical record number range, the medical record format, and the parent/child relationships between entities. Different medical record number formats are maintained throughout hospital environments.

The following is an example of a few of the different formats for medical record numbers which may be used by hospitals (each numeric value is represented by a 9, each alphabetic character by an A, and the separators are literal):

99-99-99

99/99/99

9999999

999-99-9999

A9-A9-A9

999999999999

Referring to FIG. 4, the system maintains a General Purpose Table File (GPPTABLE 313) 17 which defines the desired medical record number format in an MREDIT Table 18. FIG. 4 is the display the user accesses to define data in the table 17. The table 17 includes the following data:

Element 210 is the entity code;

Description 211 and Short Description 212 represent the name of the hospital;

The Field 213 (Field-1) contains the medical record number format (including separators);

The Field 214 (Field-2) contains the Yes/No prompt which defines whether a screen default of *CALC is used as a shortcut during the admission process in order to calculate a medical record number;

The Field 215 (Field-4) contains a sorting order for medical record reports. Additional fields are present in the table 17 to allow for future enhancements as needed.

In order to share medical record numbers in a Central Medical Records department, the following rules are followed:

All sharing entities must use the same medical record number format in their separate databases or convert them to the same format prior to sharing.

All sharing entities must share the same common files PHPUNIT 50 and PHPUIDN 3 in the M4#FILE library 103.

All sharing entities must exist within the same Central Business Office environment.

All sharing entities must use the same medical record number format defined in the MREDIT table 18 in the General Purpose Table File Maintenance 17.

All sharing entities must use the same medical record number assignment range.

Referring also to FIG. 5, the Next Medical Record Number Assignment File (GPPMRNM 312) is accessed by users through its associated file maintenance screen 19 and permits the user to assign a medical record number range, to specify the value of the next medical record number to assign, and to identify parent/child relationships. The Next Medical Record Number File Maintenance 19 controls the medical record number format and range that will be used when medical record numbers 43 are assigned to patients and edits against the MREDIT Table 18 in the General Purpose Table File (GPPTABLE 313) which is accessed by users through its associated maintenance screen 17 to maintain consistency. Medical record numbers are assigned to patients via the AR/ADT and GP file and program libraries 1 (of FIG. 1). The medical record number 43 is stored at a person and entity level in the Unit Identification Number file (PHPUIDN) 3 (of FIG. 3).

Note that the parent entity 20 in the example of FIG. 5 is "00010 Utah Medical Center". As seen in FIG. 6, the user selects the appropriate parent entity and identifies the medical record number range (using the format defined in the MREDIT Table 18 in the General Purpose Table File 17) to be used by all entities sharing patient records. The screen 51 accessed during this process contains the From MR# field 21 and the To MR# field 22 which define the medical record number range. When the user types in the number range, the format is validated against the MREDIT Table 18 in the General Purpose Table File 17. During each patient admission or registration for which a new medical record number is required, the Next MR# field 23 is updated to contain the next available Medical Record Number based on the data contained in the search processor 105 and the rules processor 104.

Existing hospitals typically have the medical record number 43 already stored in a database in a Unit Record File that is analogous to the PHPUNIT file 50 (of FIG. 3). Database operators will typically have already provided input regarding the format and content of the medical record number 43 used by the search processor 105 and the rules processor 104

(of FIG. 1) during the initial installation of the previous medical record keeping system. Generally, the same medical record format used on the preexisting system is maintained when converting to the M4#FILE 103. During the initial installation, the user generally sets file maintenance protocol to match existing formats. For example, if the previous medical record number was 99-99-99 on the preexisting foreign system, the record number will be converted and entered in the patient record identifier database 102 to be exactly the same number and format (99-99-99). In this example, reformatting is not required because the record number formats already match. As illustrated in FIG. 1, if the formats do not or cannot match, the rules processor 104 accesses a conversion program 120 that examines the original medical record number on the foreign system, maps the old number to the medical record number field in the flat file 53 residing in database 102 and reformats the number using the format defined in the MREDIT table 18 of the General Purpose Table File 17.

Referring again to FIG. 3, in an existing hospital, the new centralized medical record data file (the Unit Identification Number File PHPUIDN 3) is provided to the existing hospital as an enhancement to their existing software and also contains the standard software conversion program 120. The user runs a standard installation program, entering parameters on the screen for the release library (containing the new file PHPUIDN 3) and the preexisting file library. The installation program automatically runs the conversion program 120 and moves the new file PHPUIDN 3 to the existing file library. The conversion program 120 analyzes every record existing in PHPUNIT 50 to determine if there is a medical record number value present in the now obsolete field UMDRC. If the obsolete field UMDRC in PHPUINT 50 is blank, no record is created in the PHPUIDN file 3. If a value does exist, data is transferred from the obsolete field UMDRC in the Unit Record File (PHPUNIT) 50 to the Unit Identification Number File (PHPUIDN) 3. The value for the entity code is copied into field 4 and the Unit Reference Number field UREF# 2 in PHPUNIT 50 is copied to the IDREF# field 45 in the PHPUIDN file 3. The Identification Number Type (type of record) field IDTYPE 6 in PHPUIDN file 3 is populated with the value "MR#" to identify this record as a medical record. The Identification Number field 7 (IDIDE#) is populated with the medical record number value 43 which the conversion program 120 had transferred from the PHPUNIT file 50. Once copied, the medical record number in PHPUNIT 50 is cleared and will no longer be populated to eliminate redundant data. All system programs 100 will look to the newly populated PHPUIDN 43 to access the medical record number.

In a hospital that is new to the concept of a centralized medical records office, the present invention is implemented by utilizing the same medical record number format of any preexisting record keeping system. The user sets General Purpose Table file maintenance 17 and the Next Medical Record Number file maintenance 19 to match the existing foreign system format. For example, if the preexisting medical record number was 99-99-99 on the earlier system, the number is converted to database 102 to be exactly the same (99-99-99). A standard conversion program 120 is provided to take the demographic (including medical record number), insurance and account information from the foreign system database to flat file 53 provided in database 102 that contains the architecture of PHPUNIT 50 and PHPUIDN 3. PHPUNIT 50 is populated from the flat file 53 with all of the data except the medical record number 7. The PHPUNIT file 50 is populated first but substantially simultaneously with PHPUIDN 3.

The PHPUIDN file 3 will be populated based on logic similar to that used by an existing hospital. The conversion program 120 analyzes the foreign system to determine if there is a value in their corresponding medical record field. If the foreign system's field is blank, no record is created in PHPUIDN 3. If a value exists, a new record is created in the Unit Identification Number File (PHPUIDN) 3. The entity code value for field 4 is copied and the Unit Reference Number field (UREF#) 2 in the newly created record in PHPUNIT file 50 is copied to IDREF# field 45 in PHPUIDN file 3. The Identification Number Type field (IDTYPE) 6 in PHPUIDN 3 is populated with the value "MR#" to identify this record as a medical record number. The Identification Number field (IDIDE#) 7 is populated with the medical record number value from the foreign system. If the new hospital implementation does require a change of the record format, the conversion program 120 examines the medical record number on the foreign system, maps it to the medical record number field in the flat file 53, reformatting the number using the format defined in the General Purpose Table File's (GPPTABLE 313) MREDIT Table 18.

In the case of an existing hospital which becomes a CBO by adding a new entity, the hospital will already have all of the medical record numbers residing in the Unit Identification Number File (PHPUIDN) 3. The existing hospital becomes a parent or master entity and the parent's PHPUNIT 50 and PHPUIDN 3 files become shared files by moving these two files to M4#FILE library 103. PH#FILE 109 contains a CBO Entity field in the Location Master File which indicates that this hospital is now operating in a multiple entity environment. Once the implementation is complete, the "Sharing Entities" field 54 in the Next MR# File Maintenance display 19 can be accessed.

Two scenarios can exist when adding additional entities. If the hospital adds an existing entity having database 102, the parent hospital will run the standard conversion program 120 that will merge the new entity's PHPUNIT 50 and PHPUIDN 3 files into the now shared PHPUNIT 50 and PHPUIDN 3 files. Specific matching criteria are used to detect if the same person already exists in the shared files. The parent hospital first runs the standard conversion program 120 in "report mode" to identify potential duplicates. The report mode will create a WAS/IS file for potential duplicates between entities.

Matching criteria is used in the report mode as well as during the actual PHPUNIT/PHPUIDN file merge by examining the patient's last name, first name, birth date, medical record number, gender, and address. If the resulting data matches for at least five of the identifying criteria, a new record is not created but the child record would now become the new "IS" record. If the data does not match for at least five of the identifying criteria, a new record is created in the shared PHPUNIT 50 and PHPUIDN 3 files and is populated by copying the data from the "child's" PHPUNIT and PHPUIDN files to the "parent" or shared PHPUNIT and PHPUIDN files. The "report mode" allows both the parent and the child entities to research in advance of the file merge in order to organize or complete existing data in both environments.

The parent hospital can then run the conversion program 120 in its "merge" mode. When merging files, the same matching criteria as were used in the "report mode" are executed (last name, first name, birth date, medical record number, gender, and address). If the data matches for at least five of the identifying criteria, a new record is not created and a report is produced. If the data does not match on at least five of the identifying criteria, a new record is created in the shared PHPUNIT 50 and PHPUIDN 3 files which populated by copying the data from the "child's" PHPUNIT and PHPUIDN files to the "parent" or shared PHPUINIT 50 and PHPUIDN 3 files.

Figure 7:
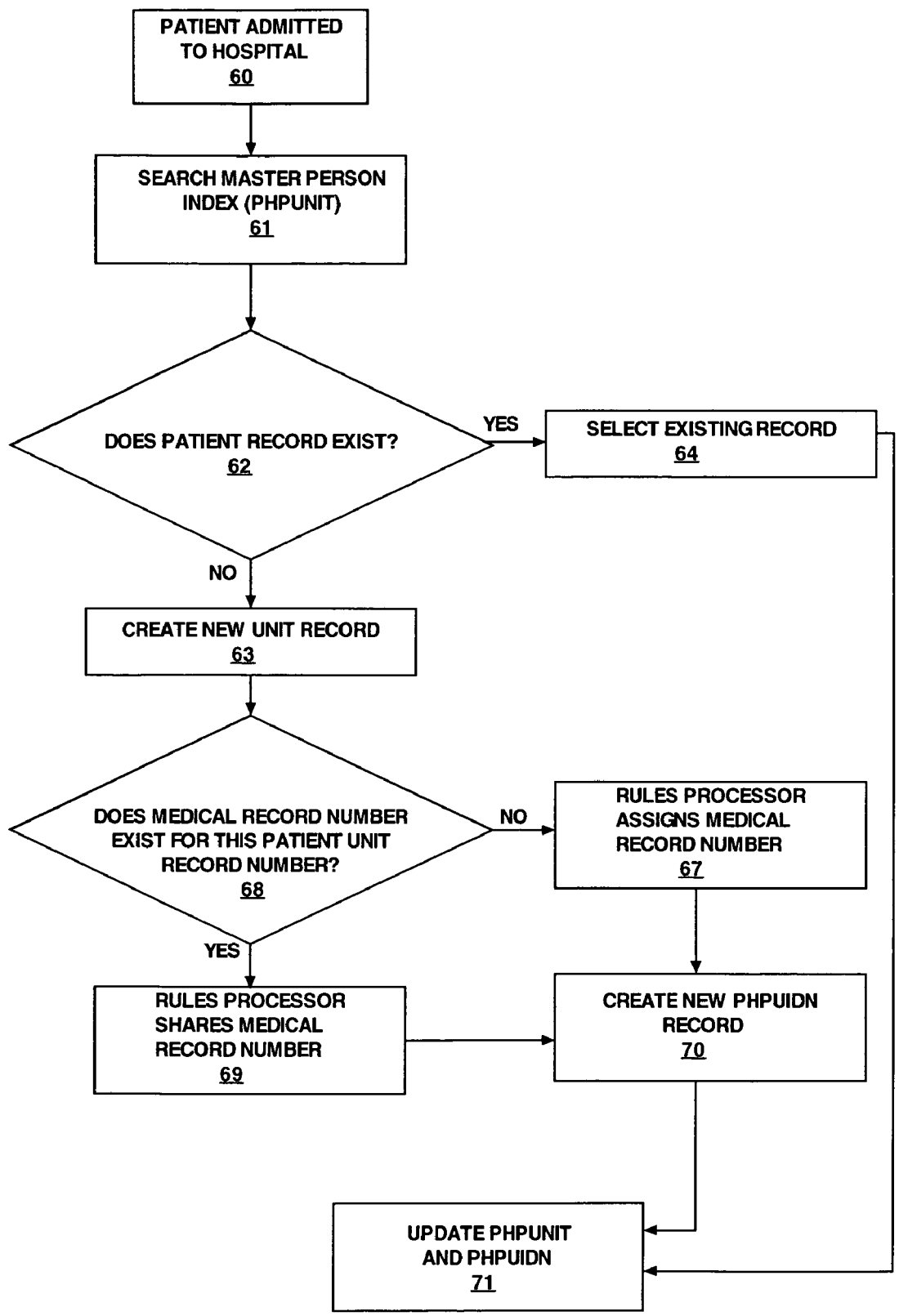
FIG. 7 is a flowchart depicting the process for adding entities to the medical record sharing system of the present invention.

As may be more readily understood by reference to FIG. 7, the shared medical record number information is accessed when an admission clerk (local or remote) registers or admits a patient to the hospital at step 60. The clerk can access the admission programs of system 100 only if he or she is authorized to access those functions. If the clerk is authorized, he or she begins at step 61 by searching the Master Person Index (PHPUNIT) 50 to see if the patient's unit record 14 already exists in the centralized database 102 as a previous patient, spouse, parent, guarantor, or other relative. The admissions program 111 knows the entity the clerk is accessing based on the entity value in the file library 109, 309 residing in the user's application library 1 list accessed when the user signs on to the system.

If, at step 62, the patient's information does not exist, the clerk creates a new unit record 14 at step 63, or if the patient's information does exist, the clerk selects the existing record from the search and select screen at step 64. FIG. 8 depicts a screen 73 via which the user may input data. While the patient's unit record is being created or updated in PHPUNIT 50, the Med Rec # field 74 can automatically default to *CALC 72 on the display screen or the user can manually type *CALC in the field 72 or the user can manually type in a literal medical record number. The function *CALC 72 or the manual entry of a medical record number begins the interrogation for a new medical record number assignment at step 68.

At step 68 the search processor 105 checks the IDIDE# field 45 of PHPUIDN 3 to determine if a medical record number 43 already exists for that patient's unique unit reference number 5 for any of the entities contained within the multiple entity organization. The rules processor 104 considers the multiple assignment scenarios discussed earlier with respect to FIG. 2. Based on those assignment rules, the rules processor 104 either shares, at step 69, the medical record number 43 attached to that patient's unique unit reference number 5 in PHPUIDN 3 by another entity, or selects, at step 67, a new number from the Next MR# (GPNEXT) field 23 located in the Next Medical Record Number Assignment File (GPPMRNM 312) 51, with user accesses as depicted in FIG. 6.

The rules processor 104 then creates a new record in PHPUIDN 3 for the entity 4 requesting the medical record number 43. The chosen medical record number 43 is placed in the IDIDE# field 7 in PHPUIDN 3. The medical record number 43 is already properly formatted regardless of its origin. This is because the medical record number 43 is stored as a formatted number in PHPUIDN 3 and is stored as a formatted number in the Next Medical Record Number Assignment File (GPPMRNM 312) 51. If the patient had previously been a patient at this facility, the previously assigned medical record number 43 will already display in the Med Rec # field 7 and a record would already exist in PHPUIDN 3 for that entity 4. The final step 71 updates the files PHPUNIT 50 and PHPUIDN 3, storing all of the data entered.

Figure 9:
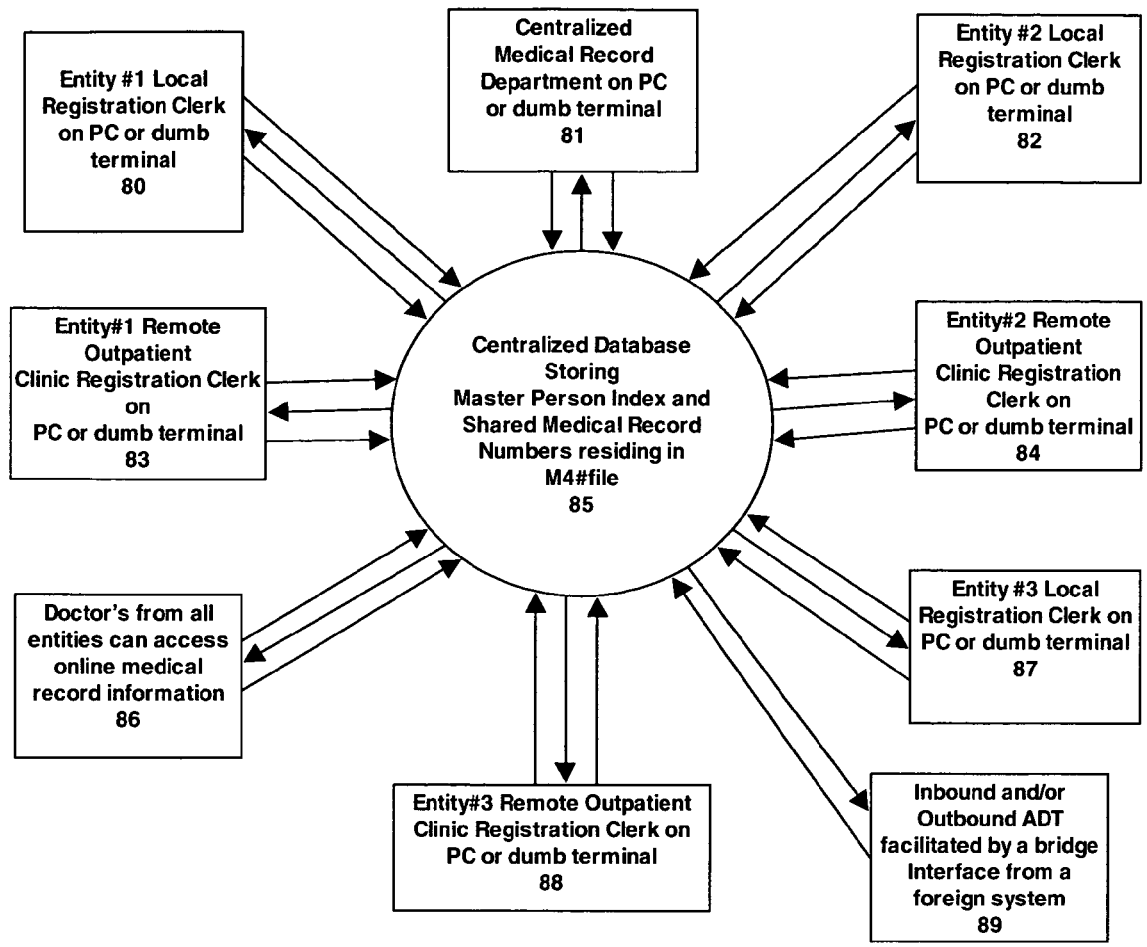
FIG. 9 is a block diagram depicting the accessing and updating of shared medical records according to the principles of the present invention.

As depicted in FIG. 9, Centralized Medical Records Department personnel 81, with the proper security, can access and update online medical record information. Authorized users (registration clerks and medical records personnel) search the master person index and request a shared medical record number from the Centralized Medical Record Database 85. They can also work with the shared medical record numbers and manage the medical record chart from any entity location 80, 82, 83, 84, 87, 88 and 89. Regardless of the entry point that begins the request or interrogation for a medical record number, the same search processor 105 and rules processor 104 are accessed and the same physical files, PHPUNIT 50, PHPUIDN 3, and GPPMRNM 312, are accessed and updated. Physicians 86 working with the medical record chart, if given the proper security, can access the online centralized medical record abstracts and medical record information. Generally doctors do not update the data, so their views of the medical record information are typically provided as display screens that do not allow the user to update any data.

When performing file maintenance for shared medical record numbers, certain conditions are automatically enforced by the record management system 100. For example, a child entity can only share medical record numbers with one parent entity. A parent entity cannot share with another parent entity. A parent entity can have multiple child entities. A parent entity cannot be deleted until the relationship to the child entities has been deleted. When a sharing entity is deleted as a parent, the actual entity record still exists; only the sharing relationship is deleted. Finally, an inactive entity record cannot be selected as a parent entity. Several examples of actual file sharing manipulations will now be discussed.

Figures 12, 13:
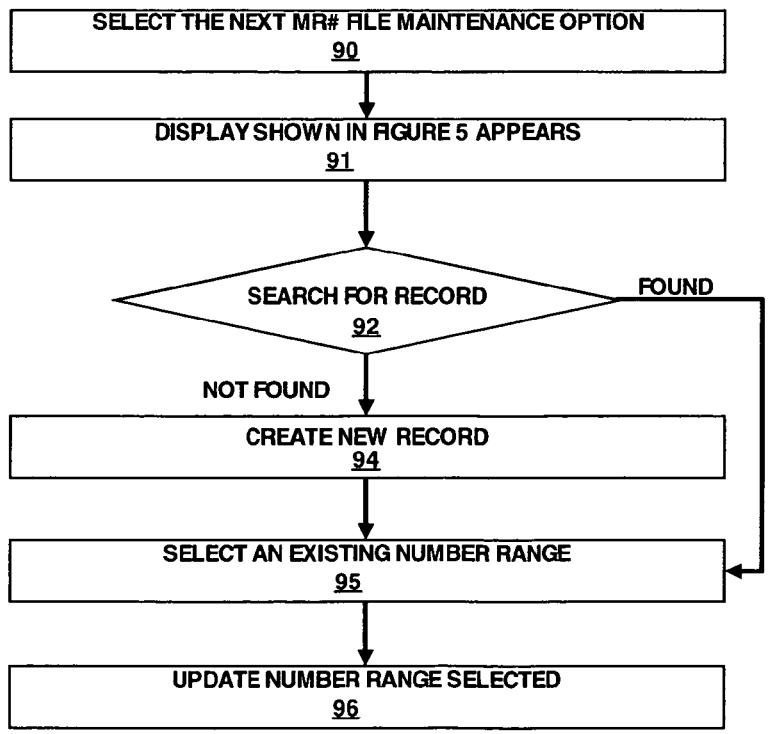
FIG. 12 is a pictorial representation of a display in which the user of the present invention may delete all medical record number ranges associated with an entity.
FIG. 13 is a flowchart depicting the procedure for adding or updating a medical record number range in accordance with the present invention.

The first example addresses the case of adding or updating a Medical Record Number Range. Referring to FIG. 13, the first step 90 is to select the Next MR# File Maintenance option which results in the user being shown, at step 91, the first Next MR# Maintenance screen 19 (FIG. 5). In FIG. 5, the Entity# field 180 refers to the number of the entity being accessed by the user. The Description field 181 contains description or name of the entity. The mnemonic of the entity is contained in the Mnem field 182. The user begins the search for a record at step 92 by typing either the entity Mnemonic (SALT in this case) or Entity Number (00020 in this case) in the 'Position to' field 183. The desired entity, or its closest match, displays on the first line 184. To work with an existing record, the user types a "2", as prompted in the options line 187, into the Opt field 186 next to the entity the user wishes to update.

If the search of step 92 is unsuccessful, the user must create a new record, at step 94, which causes the second Next MR# Maintenance screen 188 (see FIG. 18) to be displayed. Screen 188 allows multiple medical record number range entry. The user completes the field 193 with the entity mnemonic, field 190 with the beginning medical record number for the desired range and field 191 with the ending medical record number for the desired range. The user enters a number in field 192 (Next MR#) that is the same number as was entered in field 190. The rules processor program 104 increases the value in field 192 as patients are admitted.

Step 95 (FIG. 13) produces the third Next MR# Maintenance screen 194 depicted in FIG. 10, which allows the user to select an existing medical record number range. Note that whether or not a record was found at step 92, by step 95 a record exists, either because it was found during the search of step 92 or was subsequently created at step 94. To work with an existing record, the user types a "2" from the options line 187 into the Opt field 186. Referring also to FIG. 11, step 96 causes the display of the fourth Next MR# Maintenance screen 195 which allows the user to update the medical record number range selected. The user types a beginning medical record number in field 196, an ending medical record number in field 197 and again types the beginning medical record number in field 198. As patients are admitted, the rules processor program 104 will increment this value through the range specified. The last revision date for this record displays in field 199 and the user identification of the person completing the last revision displays in field 200.

Figure 14:
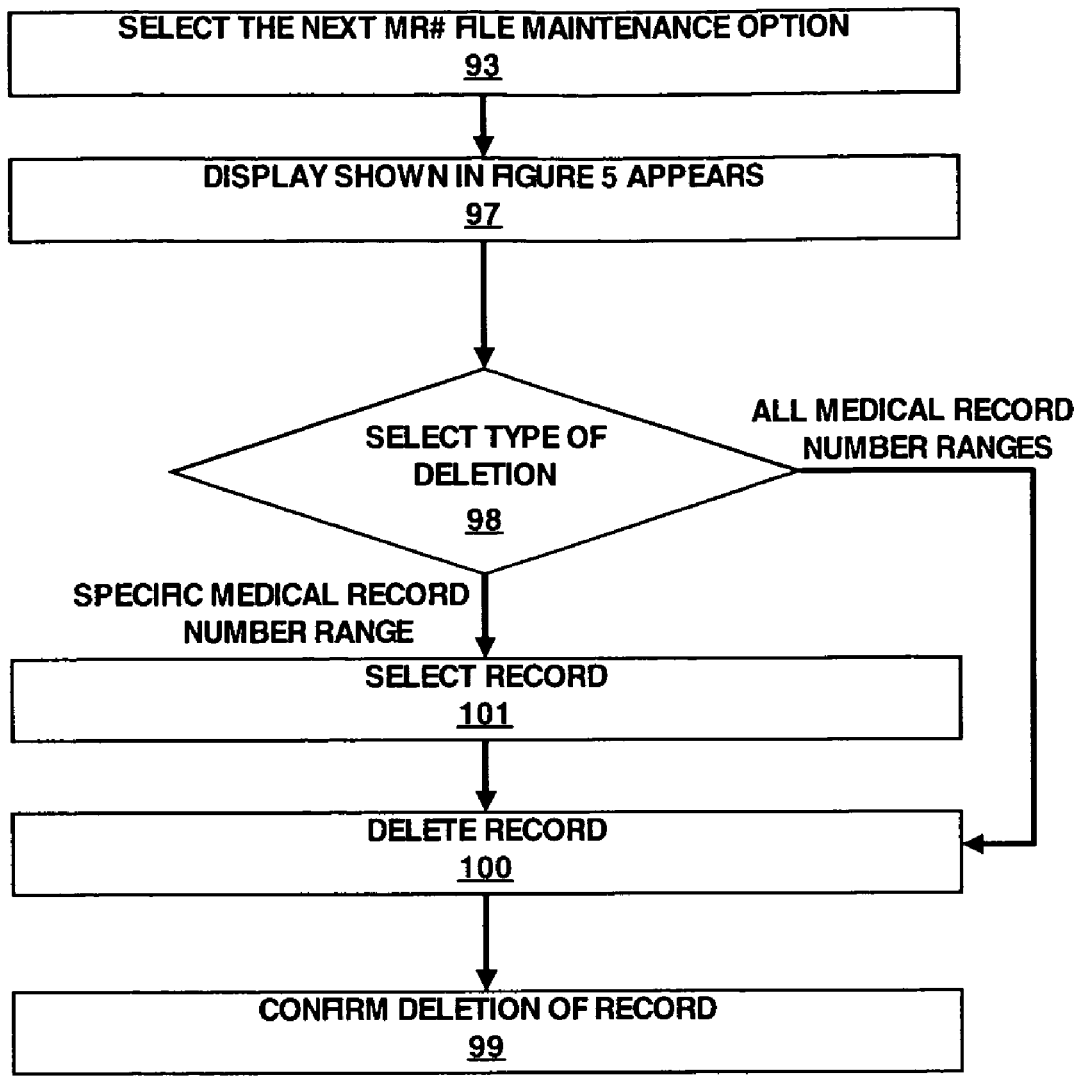
FIG. 14 is a flowchart depicting the procedure for deleting a medical record number range in accordance with the present invention.

The second example deals with deleting a medical record number range, and can be best understood by reference to FIGS. 5, 10, 12 and 14. In FIG. 14, the first step 93 is selecting the Next MR# File Maintenance option which displays, at step 97, the first Next MR# Maintenance screen 19 displays, as illustrated in FIG. 5. The third step 98 is the selection of the type of deletion to be performed. To delete all medical record number ranges for a specific entity, type a "4" from field 210 (FIG. 5) in the Opt field 186 next to the desired entity 20, for example (entity 00010 in this case). This results in the display of a 'Confirm deletion of records' window 211, as illustrated in FIG. 12. To confirm the deletion at step 99 of all record number ranges associated with that entity, as previously represented in FIG. 10, the user selects <F14> from field 212 or cancels the deletion by selecting <F12> from field 213.

To delete a specific medical record number range for an entity, the user types a "2" from field 187 into the Opt field 186 next to the desired entity. This results in the display of screen 194 (FIG. 10). The user then types a "4" from field 187 into the Opt field 186 next to the desired medical record number range. A 'Confirm deletion of records' window 211 then appears, as illustrated in FIG. 12. To confirm the deletion at step 99, the user selects <F14> from field 212 or cancels the deletion by selecting <F12> from field 213.

Figures 15, 16:
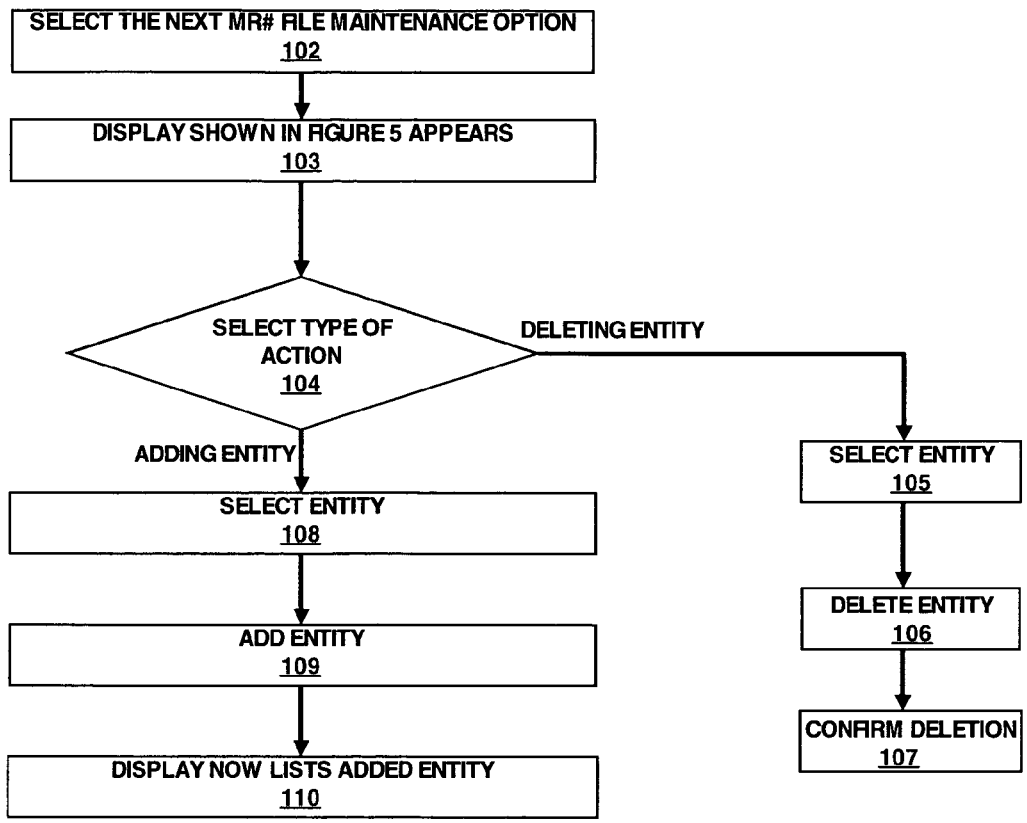
FIG. 15 is a flowchart depicting the procedure for adding or deleting a shared entity in accordance with the present invention.
FIG. 16 is a pictorial representation of a display which permits an entity search by the user of the present invention.

In order for a user to add or delete a sharing entity, the first step 102, as illustrated in FIG. 15, is to select the Next MR# file maintenance option which displays screen 19 (FIG. 5) at step 103. The sharing parent entity's number, description, and mnemonic displays in field 220 only in a multiple entity CBO environment. At step 104 the user chooses whether a sharing entity is to be added or deleted. If adding a sharing entity, the user types a "9" from field 54 into the option field 186. This produces the entity search screen 217 depicted in FIG. 16. To select the desired entity at step 108, the user types the parent entity Mnemonic or Number in the "Position to" field 218. The selected entity, or its closest match, displays on the first line 216. To add a sharing parent entity in step 109, the user types a "1" in the Opt field 186 next to the entity the user wants to assign as a parent to the selected entity. At step 110 the display 19 (FIG. 5) will then display the added entity.

To delete an assigned sharing parent entity, the user types a "4" in the Opt field 186 next to the desired child entity at step 105. By pressing <enter> at step 106 the deletion request is executed, causing the "Confirm delete of Sharing Entity" window 214, shown in FIG. 17, to appear. The confirmation of deletion at step 107 is accomplished by pressing <F14> as set forth in field 215 or cancellation of deletion by selecting <F12> from field 213.

This invention has been described with reference to certain preferred embodiments but those skilled in this field will recognize that various modifications can be made. For example, each of the display screens is only an example of how the data might be displayed, and various screens could be added or deleted depending on the needs of a particular record keeping environment. As another example, the present invention could be practiced with stand alone personal computers as part of a network, or each terminal could be a passive component connected to a single mainframe computer. The programming involved to accomplish these modifications are well within the present state of the art.

What is claimed is:

1. A central record management system for assigning a patient specific record identifier for use by a plurality of healthcare related organizations, said plurality of organizations including individual organizations potentially having an existing record identifier associated with said patient, comprising:

a search processor for determining, for a plurality of organizations, an identifier associated with a particular patient and used by an individual organization of said plurality of organizations;

a rules processor for examining determined identifiers and for assigning a patient specific record identifier for use by said plurality of organizations based on predetermined identifier allocation rules for preventing assignment of the same identifier to different patients; and a database for storing said assigned patient specific record identifier, wherein if said search processor determines a first identifier is used by a first organization for a second patient different from said particular patient and said first identifier is also used by a second organization of said plurality of organizations for said particular patient, said rules processor assigns a patient specific identifier unused by patients in said plurality of organizations.

2. A system according to claim 1, wherein said unused patient specific identifier is assigned in response to a request from said first organization initiated to support admission of said particular patient at said first organization.

3. A system according to claim 1, wherein said unused patient specific identifier is derived from at least one of, (a) a plurality of predetermined identifiers designated for assignment and (b) an identifier generator for generating identifiers based on a predetermined identifier creation method.

4. A central record management system for assigning a patient specific record identifier for use by a plurality of healthcare related organizations, said plurality of organizations including individual organizations potentially having an existing record identifier associated with said patient, comprising:

a search processor for determining, for a plurality of organizations, an identifier associated with a particular patient and used by an individual organization of said plurality of organizations;

a rules processor for examining determined identifiers and for assigning a patient specific record identifier for use by said plurality of organizations based on predetermined identifier allocation rules for preventing assignment of the same identifier to different patients; and a database for storing said assigned patient specific record identifier, wherein said search processor determines a first identifier is used by a first organization and a second identifier is used by a second organization of said plurality of organizations for said particular patient, said rules processor assigns said patient specific record identifier based on at least one of, (a) said patient specific identifier is assigned to be one of said first and said second identifiers based on a comparison of said first and said second identifiers and (b) said patient specific identifier is assigned to be one of said first and said second identifiers based on whether said identifier assignment is in response to a request from said first organization or said second organization.

5. A system according to claim 4, wherein if said search processor determines no patient specific identifier, for said particular patient, is used by said plurality of organizations, said rules processor assigns a patient specific identifier derived from at least one of, (a) a plurality of predetermined identifiers designated for assignment and (b) an identifier generator for generating identifiers based on a predetermined identifier creation method.

6. A system according to claim 4, wherein if said search processor determines a single patient specific identifier, for said particular patient, is used by one of said plurality of organizations, said rules processor assignment of said patient specific record identifier comprises adopting said single patient specific identifier for use by said plurality of organizations.

7. A system according to claim 4, wherein said request from said first organization or said second organization is initiated in response to admission of said particular patient at said first organization or said second organization.

8. A system according to claim 4, wherein if said rules processor determines said first and said second identifiers are substantially the same said rules processor assigns a patient specific identifier unused by patients in said plurality of organizations.

9. A central record management system for assigning a patient specific record identifier for use by a plurality of healthcare related organizations, said plurality of organizations including individual organizations potentially having an existing record identifier associated with said patient, comprising:
   a search processor for determining, for a plurality of organizations, an identifier associated with a particular patient and used by an individual organization of said plurality of organizations;
   a rules processor for examining determined identifiers and for assigning a patient specific record identifier for use by said plurality of organizations in response to a request from a first organization of said plurality of organizations initiated to support admission of said particular patient at said first organization, said patient specific identifier being generated based on predetermined identifier allocation rules for preventing assignment of the same identifier to different patients; and
   a database for storing said assigned patient specific record identifier, wherein if said search processor determines a first identifier is used by said first organization and a different second identifier is used by second organization of said plurality of organizations for said particular patient, said rules processor assigns said patients specific record identifier based on at least one of, (a) said patients specific identifier is assigned to be one of said first and said second identifiers based on a comparison of said first and said second identifiers and (b) said patient specific identifier is assigned to be said first identifier based on said first organization being a current admitting organization for said particular patient.

10. A system according to claim 9, wherein if said search processor determines a single patient specific identifier, for said particular patient, is used by said first organization and others of said plurality of organizations do not have an identifier for said particular patient, said rules processor assignment of said patient specific record identifier comprises adopting said single patient specific identifier for use by said plurality of organizations.

11. The system according to claim 9 further comprising a conversion program for interacting with a previous scheme of identifier format and assignment used by at least one of the first and second organizations, the conversion program adopting the scheme of identifier format and assignment whenever the scheme poses no conflict with identifier assignments made by the rules processor.

12. The system according to claim 11, wherein if the conversion program detects a conflicting identifier format adopted under the previous scheme the rules processor creates a new patient specific record identifier.

13. The system according to claim 12, wherein if the conversion program detects some conflicting identifiers adopted under the previous scheme and detects some nonconflicting identifiers adopted under the previous scheme, the conversion program merges the nonconflicting identifiers with the new patient specific record identifiers assigned by the rules processor into a single unit record file.

14. A method of managing demographic records in an organization having a plurality of entities, comprising the steps of:
   (a) creating a unit record file;
   (b) creating an identification number file;
   (c) creating application specific files;
   (d) creating a unique person specific record identifier for use by said plurality of entities that resides in the unit record file, the identification number file and each application specific file; and
   (e) searching every file for the presence of the person specific record identifier so as to link each file to all other files containing the same unique person specific record identifier.
   (f) resolving conflicts in the person specific record identifier protocol by;
      (1) assigning to a person with either no identifier or an identifier being used by another person the lowest available person specific identifier that has not already been assigned by any entity in the sharing relationship;
      (2) assigning to a person with only one identifier the existing persons specific identifier previously assigned by any entity in the sharing relationship; and
      (3) assigning to a person with a plurality of identifiers the existing person specific identifier assigned by the entity currently providing services to the person, unless none of the identifiers was assigned by the entity currently providing services, in which case the lowest existing person specific identifier will be assigned to the person.

15. The method of claim 14, further comprising the step of creating a person specific record identifier protocol adapted to create a new person specific record identifier whenever the same identifier is used to refer to different people.

16. The method of claim 15, further comprising the steps of:
   (a) creating a file sharing relationship between at least two of the entities in the organization; and
   (b) sharing a person specific record identifier found in at least one of the files with each of the files accessible to each entity in the file sharing relationship.

17. The method of claim 16, further comprising the steps of:
   (a) creating a parent/child relationship between at least two entities in the organization;
   (b) permitting all files in the child entity to be accessible to the parent entity; and
   (c) permitting at least some files in the parent entity to be accessible to the child entity.

* * * * *